United States Patent
Wang et al.

(10) Patent No.: US 9,724,431 B2
(45) Date of Patent: Aug. 8, 2017

(54) TUMOR-TARGETING MULTI-MODE IMAGING METHOD FOR LIVING BODY BASED ON GOLD NANOCLUSTERS

(71) Applicant: Southeast University, Nanjing (CN)

(72) Inventors: Xuemei Wang, Nanjing (CN); Jianling Wang, Nanjing (CN); Qiwei Li, Nanjing (CN); Hui Jiang, Nanjing (CN)

(73) Assignee: SOUTHEAST UNIVERSITY, Nanjing (CN)

( * ) Notice: Subject to any disclaimer, the term of this patent is extended or adjusted under 35 U.S.C. 154(b) by 316 days.

(21) Appl. No.: 14/567,972

(22) Filed: Dec. 11, 2014

(65) Prior Publication Data

US 2015/0093332 A1  Apr. 2, 2015

Related U.S. Application Data

(63) Continuation of application No. PCT/CN2013/070928, filed on Jan. 24, 2013.

(30) Foreign Application Priority Data

Jun. 11, 2012 (CN) .......................... 2012 1 0190242

(51) Int. Cl.
| | |
|---|---|
| *A61K 49/00* | (2006.01) |
| *A61K 49/22* | (2006.01) |
| *A61B 8/08* | (2006.01) |
| *G01N 29/00* | (2006.01) |
| *G01N 33/50* | (2006.01) |
| *G01N 33/58* | (2006.01) |
| *A61B 5/00* | (2006.01) |
| *G01N 21/64* | (2006.01) |
| *G01N 21/65* | (2006.01) |

(52) U.S. Cl.
CPC ........ *A61K 49/0002* (2013.01); *A61B 5/0071* (2013.01); *A61K 49/0017* (2013.01); *A61K 49/0065* (2013.01); *A61K 49/0093* (2013.01); *A61K 49/22* (2013.01); *A61K 49/222* (2013.01); *G01N 21/6486* (2013.01); *G01N 29/00* (2013.01); *G01N 33/5005* (2013.01); *G01N 33/582* (2013.01); *A61B 8/085* (2013.01); *A61B 8/481* (2013.01); *G01N 21/6458* (2013.01); *G01N 21/65* (2013.01)

(58) Field of Classification Search
None
See application file for complete search history.

(56) References Cited

U.S. PATENT DOCUMENTS

| | | | |
|---|---|---|---|
| 2010/0009427 A1 | 1/2010 | Martinez et al. | |
| 2010/0172997 A1* | 7/2010 | Omary ................ | A61K 9/5115 424/489 |
| 2011/0300532 A1 | 12/2011 | Jahnen Dechent et al. | |

FOREIGN PATENT DOCUMENTS

| | | |
|---|---|---|
| CN | 102150034 A | 8/2011 |
| CN | 102366632 A | 3/2012 |
| CN | 102735752 A | 10/2012 |
| WO | WO 2010/016803 | 2/2010 |

OTHER PUBLICATIONS

Hua He et al., "Nonbleaching Flurescence of Gold Nanoparticles and Its Applications in Cancer Cell Imaging" Analytical Chemitry, vol. 80, No. 15, Aug. 1, 2008, pp. 5951-5957.
International Search Report Appl No. PCT/CN2013/070928, dated May 2, 2013.
Wang, Jianling, et al., "In vivo Delf-bio-imaging of tumors through in situ biosynthesized fluorescent gold nanoclusters", Scientific Reports, 3:1157, (2013) 6 pages.
Wu, Xu, "Tumor in Vivo Fluorescence and Photodynamic Therapy Based on Nanomaterials", A thesis submitted in partial satisfaction of the Requirements for the degree of Master of Science in Biochemistry and molecular biology in the Graduate School of Hunan University (1997), 81 pages.
Wu, Xu et al., "Ultrasmall near-infrared gold nanoclusters for tumor fluorescence imaging in vivo", The Royal Society of Chemistry 2010, Nanoscale, 2010, 2, pp. 2244-2249.
Yuan, Yuan et al. "Live Cells Fluorescence Imaging by Bovine Serum Albumin-mediated Synthesized Gold Nanoclusters" Chemical Journal of Chinese Universities, vol. 31, No. 11 (2010), 6 pages.

\* cited by examiner

*Primary Examiner* — Michael G Hartley
*Assistant Examiner* — Jennifer Lamberski
(74) *Attorney, Agent, or Firm* — Knobbe Martens Olson and Bear LLP

(57) ABSTRACT

A tumor-targeting multi-mode imaging and analyzing method for living body based on gold nanoclusters can include incubating the relevant cells with chloroauric acid and the salt solution thereof with certain concentration under physiological conditions, thereby generating gold nanoclusters. After, real-time non-invasive fluorescence imaging, Raman imaging and/or ultrasonic imaging can be used to image the tumor tissue.

16 Claims, No Drawings

TUMOR-TARGETING MULTI-MODE IMAGING METHOD FOR LIVING BODY BASED ON GOLD NANOCLUSTERS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTIONS

The present disclosure relates to the technical fields of tumor detection and treatment, including methods for preparing and using tumor-targeting nanoprobes.

BACKGROUND

Tumors, especially malignant cancerous tumors, are the leading cause of death in humans. Although tumor biology and medical oncology has been greatly developed, such as through the discovery of tumor biomarkers, convenient surgical procedures, and development of radiotherapy and chemotherapy, overall cancer survival has not had significant improvement. In order to improve survival rates and the quality of life of patients suffering with cancer, we have continued to develop new methods for early diagnosis and treatment of cancer.

Today, there is a great challenge in the development of tumor-targeting nanoprobes. Compared with the most conventional method in the field of oncology, it is possible for molecular imaging to detect progression of the disease or treatment efficacy earlier. Fluorescence imaging and Raman imaging draw special attention from medical diagnosis, owing to their high sensitivity, and could provide quantitative and dynamic bioinformation. With the continuous deepening of study and improvement of the system, fluorescence imaging and Raman imaging techniques can quickly measure tumor growth of a variety of cancer models, as well as timely observe and assess changes of cancer cells during cancer treatment. Further, they may quantitatively detect in situ tumors, metastatic tumors, and/or spontaneous tumors in mice as a whole.

For example, Hollingshead et al. constructed U251-HRE cells using human glioma cell line U251, and implanted this tumor cell into nude mice. They found that when tumors reached 300-500 mg, hypoxia occurred in local tissue. At this point, a significant expression of luciferase can be monitored. This method not only monitored the tumor itself, but more importantly could monitor the microenvironment where tumor cells are located. Additionally, fluorescence imaging and Raman imaging techniques can provide precise information of molecular characteristics and changes of cells and tissues, and can reveal histomorphologic and anatomical details through spectral fingerprints of molecular structure and location. Thereby, they can serve as clinical diagnostic tools to help medical professionals detect disease and response to treatment at the molecular level.

Developments in nanoscience and nanotechnology has facilitated the advancement of nanomaterials used for molecular imaging and cancer therapy, and has promoted the development of nanodevices for use in cancer detection and screening. Moreover, nanomaterials can not only provide highly sensitive and specific imaging information of cancer patients, but can also deliver anticancer drugs to site of the tumor. In addition, some of nanomaterials themselves can be used as drugs for treatment of cancer. However, our understanding on the following areas is still limited: biomarkers suitable for imaging; selection of materials for imaging target and contrast enhancement; and chemical methods used for imaging of bioprobes. We have also encountered difficulties in the development of cancer-specific imaging agents, including: suboptimal transport of probes targeting tissue or tumor; great biological toxicity; poor stability of the probe; low intensity of in vivo signal enhancement.

DETAILED DESCRIPTION

The object of the present disclosure is to provide a nano-bio-probe of gold nanoclusters, which can be produced by in situ growth, and to integrate multiple functions including in vivo or ex vivo tumor targeting, fluorescence, enhanced Raman information, and ultrasound imaging. Also disclosed is an innovative method which can be used for tumor targeting fluorescence imaging, Raman imaging, and ultrasound imaging of living tumor cells or in vivo. For example, in some embodiments the imaging can be used to determine the size and site of a tumor. Additionally, a treatment course and post-treatment recovery process can be monitored by ultrasound imaging. Furthermore, according to the distribution and intensity of fluorescence of fluorescence imaging, as well as position of the wave number and the intensity of Raman signal in Raman spectrum of Raman imaging, qualitative and quantitative analysis of the distribution and number of biochemical components of the tumor area could be carried out so as to achieve early diagnosis of tumor and timely monitoring of tumor treatment course.

Through in situ growth of nano-bio-probes, such as gold nanoclusters, with tumor-targeting molecular imaging at lesions of the living body, the probes can achieve multiple functions such as tumor targeting, fluorescence imaging, Raman imaging, and ultrasound imaging, and achieve synchronization of monitoring multi-modes. Furthermore, this in situ in vivo imaging method may be used not only in the early diagnosis of tumors, but also can be used for timely monitoring during cancer treatment.

Accordingly, disclosed herein are embodiments of a tumor-targeting multi-mode imaging and analyzing method for living body based on gold nanoclusters. The gold nanoclusters can be generated by incubating cells with chloroauric acid and the salt solution thereof with certain concentration under physiological conditions. Once generated, the gold nanoclusters can be used for realizing real-time non-invasive fluorescence imaging, Raman imaging, and ultrasonic imaging of tumor cells with high resolution. Based on this, a local subcutaneous injection method was adopted, and real-time in-situ living body tumor-targeting fluorescence imaging, Raman imaging, and ultrasonic imaging were realized on tumor-transplantation nude mouse models. With the functional nano-scale probes, multiple functions of tumor targeting, fluorescence imaging, Raman imaging, and ultrasonic imaging being combined, synchronous monitoring of multiple modes can be achieved. Meanwhile, with the in-situ living body imaging method based on gold nanoclusters, accurate positioning and tumor-targeting imaging and analysis can be realized.

Disclosed herein is an in vivo tumor targeting multi-mode imaging method based on gold nanoclusters. The first step of the method can include incubating chloroauric acid or its salt solution and tumor cells to form a large amount of gold nanoclusters, which can be specifically generated in tumor cells. Following, high-resolution microscopic imaging of tumor cells can be carried out using a fluorescence microscope, Raman microscopy, or ultrasound imaging technique. Qualitative or quantitative analysis of cellular structure or chemical components can then be performed through ultrasound imaging, the distribution and intensity of fluorescence of fluorescence imaging, and/or the wave number and the intensity of Raman signal in Raman spectrum of Raman imaging.

Some examples are disclosed below:

First, an embodiment of a method can be carried out at the cellular level, including the following steps:

1) Hepatoma HepG2 and leukemia K562 cells can be selected as research subjects. In some embodiments, these two types of cells can be incubated with 1-1000 μmol/L of chloroauric acid or its salt solution in cell incubator for 16 to 48 hours, respectively, so as to form gold nanoclusters through in-situ biosynthesis.

2) For HepG2 (K562), the cells can be incubated with 1-1000 μmol/L of chloroauric acid or its salt sterile solution for 16 to 48 hours to form a distribution of gold nanoclusters in the cells. The gold nanoclusters can be advantageous for imaging as they can have good biocompatibility. The gold nanoclusters can be characterized using a fluorescence microscope or Raman microscopy. The gold nanoclusters grown in situ inside tumor cells can be explored using fluorescence imaging and Raman imaging of tumor targeting among living tumor cells. Afterwards, qualitative or quantitative analysis can be performed to examine cellular structure or chemical components, and the analysis can be performed through ultrasound imaging, the distribution and intensity of fluorescence of fluorescence imaging, and/or the position of the wave number and the intensity of Raman signal in Raman spectrum of Raman imaging.

When this imaging method is used for in vivo tumor imaging, chloroauric acid or its salt solution can be injected into the surrounding area of the tumor tissue or into the tumor tissue to generate a large amount of gold nanoclusters from the tumor cells. Raman imaging or fluorescence imaging can then be carried out for the tumor area using a Raman imager or an in vivo fluorescence imager. Ultrasound imaging may be used to determine the size and site of the tumor, as well as to monitor treatment course and post-treatment recovery process. Additionally, according to the intensity and distribution of Raman signal and fluorescence signal, qualitative and quantitative analysis of the distribution and number of biochemical components of the tumor area could be carried out.

Methods can be carried out at in vivo animal models level, and specific steps are as follows:

1) A nude mice model transplanted with hepatoma can be constructed.

2) 0.1-0.5 mL of 1-1000 mmol/L of sterile chloroauric acid or its salt solution can be injected subcutaneously around the tumor, and after incubation for 12 to 36 hours, gold nanoclusters integrating multiple functions such as tumor targeting, fluorescence imaging, Raman imaging, and ultrasound imaging, can be generated in situ within the tumor tissue.

3) Using the gold nanoclusters generated in Step 2), Raman or fluorescence imaging of tumor area can be carried out with Raman imaging or fluorescence imaging technique. Ultrasound imaging may be used to determine the size and site of the tumor, as well as to monitor treatment course and post-treatment recovery process. Additionally, according to the intensity and distribution of Raman signal and fluorescence signal, qualitative and quantitative analysis of the distribution and number of biochemical components of the tumor area could be carried out.

The present disclosure has the following advantages and effects as compared with the existing technical methods. In the present disclosure, a method of nano-bio-probe such as gold nanoclusters for multifunctional molecular imaging grown in situ within living body can be used. This method can avoid biotoxicity caused by chemicals agents and nanomaterials stabilizers introduced during conventional synthesis of nanomaterials. Further, the method can avoid the disadvantage that traditional nanomaterials are prone to be trapped by the reticuloendothelial system, so as to be cleared and not be able to reach the lesion tissue in order to achieve in vivo tumor targeting fluorescence, Raman and ultrasound imaging. Moreover, the functional nanoprobes can integrate multiple functions including, for example, tumor targeting, fluorescence imaging, Raman imaging, and ultrasound imaging, and can enable synchronous monitoring of multimodes. This in situ in vivo imaging method can be used in the timely multifunction imaging of clinical diagnosis of tumor, so as to achieve early diagnosis of tumor and timely tracking during tumor treatment.

In some embodiments, the disclosed method for ex vivo imaging of tumor cell can be as follows: incubating chloroauric acid or its salt solution and tumor cells which can generate a large amount of gold nanoclusters generated in the tumor cells, and then analyzing cellular structure or chemical components of tumor cells with fluorescence imaging, Raman imaging or ultrasound imaging technique.

In some embodiments, the method for in vivo imaging of tumor can be as follows: injecting chloroauric acid or its salt solution into the surrounding areas of the tumor tissue or into the tumor tissue itself to form a large amount of gold nanoclusters generated in the tumor cells, and analyzing the distribution and number of biochemical components of the tumor cells with Raman imaging and/or in vivo fluorescence imaging techniques.

To achieve the above objects, the present disclosure adopts the following technical measures:

First, methods can be carried out at the cellular level, and the specific steps can be:

1) Hepatoma HepG2 and leukemia K562 cells can be selected as research subjects. These two types of cells can be incubated with 1-1000 μmol/L of chloroauric acid or its salt solution in a cell incubator for 16 to 48 hours to produce gold nanoclusters through in-situ biosynthesis.

2) For HepG2 (K562), the cells can be incubated with 1-1000 μmol/L of chloroauric acid or its salt sterile solution for 16 to 48 hours to form gold nanoclusters, and the distribution of gold nanoclusters in the cell can be characterized using a fluorescence microscope. Further, a fluorescence microscope or Raman microscopy can be used to explore the gold nanoclusters grown in situ inside tumor cells. Fluorescence imaging and Raman imaging of tumor targeting can be used among living tumor cells. Additionally, qualitative or quantitative analysis of cellular structure or chemical components can be performed through ultrasound imaging. This can include the distribution and intensity of fluorescence of fluorescence imaging, as well as the position of the wave number and the intensity of Raman signal in Raman spectrum of Raman imaging.

Methods can be carried out with in vivo animal models, and specific steps were as follows:

1) A nude mice model transplanted with hepatoma can be constructed.

2) 0.1-0.5 mL of 1-1000 mmol/L of chloroauric acid or its salt sterile solution can be injected subcutaneously around the tumor, and after incubation for 12 to 36 hours, gold nanoclusters integrating multiple functions such as tumor targeting, fluorescence imaging, Raman imaging, and ultrasound imaging can be generated in situ within the tumor tissue.

3) Using gold nanoclusters generated in Step 2), Raman or fluorescence imaging of tumor area can be carried out with Raman imaging or fluorescence imaging technique. Ultrasound imaging can be used to determine the size and site of the tumor, as well as to monitor treatment course and post-treatment recovery process. Additionally, according to the intensity and distribution of Raman and fluorescence signal, qualitative and quantitative analysis of distribution and number of biochemical components of the tumor area could be carried out, so as to realize early diagnosis of tumor and timely monitoring of tumor treatment course.

In some embodiments, an imaging method based on gold nanoclusters biosynthesized in situ within cells is disclosed.

First, 1-1000 mmol/L of chloroauric acid or its salt sterile solution can be incubated with HepG2 cells for 16-48 hours (37° C., 5% $CO_2$, RH 95%), to obtain gold nanoclusters biosynthesized in situ in vivo. Then medium in the petri dish can be removed carefully, and cells can be gently washed with sterile PBS at pH 7.2 and then placed under laser focal fluorescence microscope. Green fluorescent image of cells could be captured through motivation with blue light at 488 nm. It could be clearly observed with fluorescence tomography that these gold nanoclusters mainly concentrate in the cell nucleus area.

In some embodiments, a tumor targeting imaging methods based on gold nanoclusters grown in situ within living lesion is disclosed.

First, 0.1-0.5 mL of 1-1000 mmol/L of chloroauric acid or its salt sterile solution could be injected subcutaneously around the tumor in nude mice model transplanted with hepatoma. After incubation for 12 to 36 hours, these experimental nude mice could be anesthetized with 5% isoflurane gas. Then they could be placed on small animals in vivo imaging instrument platform. Images of the tumor area could be captured by simply selecting Blue-ray motivation.

What is claimed is:

1. A tumor-targeting imaging method for a living body based on gold nanoclusters, the method comprising:
    incubating chloroauric acid or its salt solution with tumor cells in the living body to form gold nanoclusters;
    performing high-resolution microscopic imaging of the tumor cells, wherein the imaging is selected from the group consisting of a fluorescence microscope, Raman microscopy, and an ultrasound imaging technique; and
    analyzing cellular structure or chemical components from the imaging.

2. A tumor-targeting imaging method for a living body based on gold nanoclusters, the method comprising:
    injecting chloroauric acid or its salt solution into the living body in areas surrounding tumor tissue or into the tumor tissue itself, thereby generating gold nanoclusters in tumor cells;
    imaging the tumor tissue and the areas surrounding the tumor tissue, wherein the imaging is selected from the group consisting of Raman imaging, fluorescence imaging, and ultrasound imaging to form an image; and
    analyzing the image to determine the size and location of the tumor or to monitor treatment course and post-treatment recovery process.

3. A method for analyzing cancerous tissue in a patient comprising:
    combining chloroauric acid, or its salt solution, with tumor cells in a patient;
    incubating the chloroauric acid, or its salt solution, with the tumor cells to form gold nanoclusters in the patient;
    imaging the gold nanoclusters; and
    analyzing characteristics of the gold nanoclusters and the tumor tissues.

4. The method of claim 3, wherein imaging is selected from the group consisting of fluorescence microscopy, Raman microscopy, and ultrasound imaging.

5. The method of claim 4, further comprising synchronous monitoring of a plurality of imaging techniques.

6. The method of claim 3, wherein combining comprises injecting the chloroauric acid, or its salt solution, into the tumor cells or tissue surrounding the tumor cells.

7. The method of claim 3, wherein biotoxicity is avoided.

8. The method of claim 3, wherein the gold nanoclustors are not trapped or cleared by the reticuloendothelial system.

9. The method of claim 3, further comprising diagnosing a tumor.

10. The method of claim 3, wherein the distribution of intensity of a fluorescence is analyzed.

11. The method of claim 3, wherein the wave number and intensity of a Raman signal in a Raman spectrum is analyzed.

12. The method of claim 3, wherein combining comprises combining 0.1-0.5 mL of 1-1000 mmol/L chloroauric acid, or its salt solution with the tumor cells.

13. The method of claim 3, wherein analyzing comprises determining the size and site of the tumor cells.

14. The method of claim 3, wherein analyzing comprises monitoring a tumor treatment course.

15. The method of claim 3, wherein the tumor cells can be hepatoma or leukemia cells.

16. The method of claim 3, wherein incubating lasts from 16-48 hours.

* * * * *